US00PP16377P3

(12) United States Plant Patent
Miyazaki et al.

(10) Patent No.: US PP16,377 P3
(45) Date of Patent: Mar. 28, 2006

(54) ***VIOLA CORNUTA* PLANT NAMED SUNVIOHO**

(50) Latin Name: *Viola cornuta*
Varietal Denomination: Sunvioho

(75) Inventors: Kiyoshi Miyazaki, Hikone (JP); Naoto Takamura, Omihachiman (JP); Yukihiro Ikeda, Akashi (JP)

(73) Assignee: Suntory Flowers Limited, Tokyo (JP)

( * ) Notice: Subject to any disclaimer, the term of this patent is extended or adjusted under 35 U.S.C. 154(b) by 157 days.

(21) Appl. No.: 10/611,354

(22) Filed: Jun. 30, 2003

(65) Prior Publication Data

US 2005/0076416 P1 Apr. 7, 2005

(30) Foreign Application Priority Data

Dec. 26, 2002 (JP) ..... 15367

(51) Int. Cl.
*A01H 5/00* (2006.01)

(52) U.S. Cl. ..... Plt./323

(58) Field of Classification Search ..... Plt./323
See application file for complete search history.

(56) References Cited

PUBLICATIONS

Catalogue for Profit Organization, 2002 Fall–2003 Spring, No. 78, 4 pages, Published by Sakata Seed Co., Japan, May 2002 with English explanation.

Catalogue for Profit Organization, 2002–2003, 5 pages, Published by Takii Seed Co., Japan, Apr. 2002 with English explanation.

*Primary Examiner*—Howard J. Locker
(74) *Attorney, Agent, or Firm*—Christie, Parker and Hale, LLP

(57) ABSTRACT

Disclosed herein is new *Viola cornuta* plant named 'Sunvioho', which is a vegetative propagated variety that was developed by specific hybridization between '9V-39a' and 'Alpine Sun'. 'Sunvioho' has a spreading habit with very long stem. The plant height is low and the branching is abundant. Flowers are vertically oblong and very small. The color of flower is pale yellow green with vivid yellow eye. The plant has a high resistance to rain, cold, pests and diseases.

2 Drawing Sheets

Botanical/commercial classification: *Viola cornuta/Viola* Plant.

Varietal denomination: cv. 'Sunvioho'.

BACKGROUND OF THE VARIETY

The genus *Viola* is included in the family Violaceae and has about 500 species of annuals, biennials, evergreen, and semi-evergreen and deciduous perennials found in varied habitats in temperate regions worldwide.

Each flower has 5 petals: a spurred lower petal, 2 lateral petals and 2 upward-facing upper petals.

While many cultivars within the genus are informally referred to as garden pansies, *violas* are all derived from the complex hybridization of *V. tricolour, V. lutea, V. cornuta,* and other species.

*Viola cornuta* has played an important role in the development of garden *violas* and violettas as a result of cross breeding with the garden pansy *V. wittrocklana.*

*Viola cornuta* is stem prostrate, with leaves narrow to broad ovate, base cordate to truncate, and margin shallow-crenate.

The female parent used in the crossing of 'Sunvioho' was '9V-39a' (unpatented in the U.S.) which is our breeding line and grown at Omori-cho, Yokaichi-shi, Shiga-ken, Japan The pollen parent used in the crossing of 'Sunvioho' was 'Alpine Sun' (a cultivar unpatented in the U.S.).

BREEDING PROCESS

Crossing between '9V-39a' as female parent and 'Alpine Sun' as male parent was conducted at Omori-cho, Yokaichi-shi, Shiga-ken, Japan in April 2000. In May, seeds were obtained from the crossing and were sown and grown at the same location. In August, three seedlings were selected in view of having highly spreading habit with white petals from 20 seedlings obtained, and propagated by cutting. Those three seedlings were tested by flower potting and bedding from October 2001, at Omori-cho, Yokaichi-shi, Shiga-ken, Japan. Finally one variety was selected in view of having a long blooming time. The botanical characteristics of that plant were then examined, using similar variety 'Violetto Nive' (unpatented in the U.S.) and 'Alpine Summer' (unpatented in the U.S.) for comparison. As a result, it was concluded that this *Viola cornuta* plant is distinguishable from any other variety, whose existence is known to us, and uniform and stable in its characteristics. The new variety of *Viola cornuta* plant was named 'Sunvioho'.

*Viola cornuta* plants, 'Alpine Sun' and '9V-39a', are presently maintained at Omori-cho, Yokaichi-shi, Shiga-ken, Japan.

This new and distinct variety of *Viola cornuta* plant, 'Sunvioho', was asexually reproduced by tissue culture at the aforementioned the Omori-cho, Yokaichi-shi, Shiga-ken, Japan and the homogeneity and stability thereof were confirmed.

The new variety reproduces true to type in successive generations of asexual reproduction.

DESCRIPTION

In the following description, the color-coding is in accordance with the Horticultural Colour Chart of The Royal Horticultural Society, London, England (R.H.S. Colour Chart).

The botanical characteristics of the female parent plant '9V-39a' used in the crossing of 'Sunvioho' are as follows.

Plant:
*Stemmed or non-stemmed.*—Stemmed.
*Growth habit.*—Spreading.
*Height.*—Approximately 9 cm.
*Plant cover.*—Approximately 49 cm.
Stem:
*Length.*—Approximately 36 cm.
*Branching.*—Much.
*Pubescence.*—Present.
Leaf:
*Overall form.*—Narrow elliptic.
*Apex form.*—Acute.
*Base form.*—Acute.
*Margin.*—Slightly lobed.
*Length.*—Approximately 1.9 cm.
*Width.*—Approximately 1.2 cm.
*Color of upper surface.*—Grayish olive green (Near R.H.S. 137A).
*Color of under surface.*—Moderate yellow green (Near R.H.S. 137C).
*Variegation.*—Absent.
*Leaf luster.*—Lustrous.
*Vein.*—Distinct.
*Petiole length.*—Approximately 1.4 cm.
*Stipule length.*—Approximately 1.8 cm.
Flower:
*Peduncle length.*—Approximately 7.5 cm.
*Peduncle thickness.*—Thin.
*Peduncle color.*—Strong yellow green (Near R.H.S. 144B).
*Flower form.*—Vertically oblong.
*Flowering direction.*—Upward.
*Longitudinal diameter.*—Approximately 3.2 cm.
*Horizontal diameter.*—Approximately 3.0 cm.
*Ruffle of petal margin.*—Weakly ruffled.
*Petal curving.*—Very weak.
*Petal number.*—Single.
*Upper petal.*—Form — Round. Size — Approximately 1.6×1.6 cm. Petal color — Single-colored. Ground color — Pale yellow green (Near R.H.S. 157A). Blotch — Absent.
*Side petal.*—Form — Ovate. Size — Approximately 1.3×1.5 cm. Petal color — Single-colored. Ground color — Pale yellow green (Near R.H.S. 157A). Blotch — Absent.
*Lower petal.*—Form — Cordate. Size — Approximately 1.9×1.9 cm. Petal color — Single-colored. Ground color — Pale yellow green (Near R.H.S. 157A). Blotch — Absent.
*Eye color.*—Vivid reddish yellow (Near R.H.S. 14A).
*Eye size.*—Medium.
*Thickness of petal.*—Medium.
*Spur length.*—Longer than the sepal appendage.
*Sepal.*—Short.
*Number of flowers.*—Many.
Seed:
*Color.*—Deep brown.
Physical property:
*Flowering time.*—Late.
*Fragrance.*—Faint.
*Resistance.*—Rain — Strong. Cold — Strong. Heat — Medium. Disease — Strong. Pest — Strong.

The botanical characteristics of the male parent plant 'Alpine Sun' used in the crossing of 'Sunvioho' are as follows.

Plant:
*Stemmed or non-stemmed.*—Stemmed.
*Growth habit.*—Spreading.
*Height.*—Approximately 8 cm.
*Plant cover.*—Approximately 35 cm.
Stem:
*Length.*—Approximately 25 cm.
*Branching.*—Much.
*Pubescence.*—Present.
Leaf:
*Overall form.*—Narrow elliptic.
*Apex form.*—Obtuse.
*Base form.*—Acute.
*Margin.*—Serrated or slightly lobed.
*Length.*—Approximately 2.1 cm.
*Width.*—Approximately 1.0 cm.
*Color of upper surface.*—Grayish olive green (Near R.H.S. 137A).
*Color of under surface.*—Moderate yellow green (Near R.H.S. 137C).
*Variegation.*—Absent.
*Leaf luster.*—Matte.
*Vein.*—Apparent.
*Petiole length.*—Approximately 2.2 cm.
*Stipule length.*—Approximately 2.1 cm.
Flower:
*Peduncle length.*—Approximately 8.0 cm.
*Peduncle thickness.*—Thin.
*Peduncle color.*—Strong yellow green (Near R.H.S. 144B).
*Flower form.*—Vertically oblong.
*Flowering direction.*—Upward.
*Longitudinal diameter.*—Approximately 3.3 cm.
*Horizontal diameter.*—Approximately 2.5 cm.
*Ruffle of petal margin.*—Flat.
*Petal curving.*—Weak.
*Petal number.*—Single.
*Upper petal.*—Form — Round. Size — Approximately 1.1×1.0 cm. Petal color — Single-colored. Ground color — Vivid yellow (Near R.H.S. 9B). Blotch — Absent.
*Side petal.*—Form — Ovate. Size — Approximately 1.2×1.0 cm. Petal color — Single-colored. Ground color — Vivid yellow (Near R.H.S. 9B). Blotch — Absent.
*Lower petal.*—Form — Cordate. Size — Approximately 1.4×1.3 cm. Petal color — Single-colored. Ground color — Vivid yellow (Near R.H.S. 9A). Blotch — Absent.
*Eye color.*—Vivid yellow (Near R.H.S. 13A).
*Eye size.*—Small.
*Thickness of petal.*—Thin.
*Spur length.*—Longer than the sepal appendage.
*Sepal.*—Short.
*Number of flowers.*—Many.
Seed:
*Color.*—Deep brown.

Physical property:
*Flowering time.*—Late.
*Fragrance.*—Absent.
*Resistance.*—Rain — Medium. Cold — Strong. Heat — Medium. Disease — Strong. Pest — Strong.

SUMMARY OF THE NEW VARIETY

The new variety of *viola* plant named 'Sunvioho', which is a vegetative propagated variety, has a spreading plant habit with very long epigeal stem. The plant height is low and the branching is abundant. The flowers of the new variety are oblong and very small, and the color of flower is pale yellow green with vivid yellow eye. The new variety has a high resistance to cold, pests and diseases.

DESCRIPTION OF THE VARIETY

Figure 1:
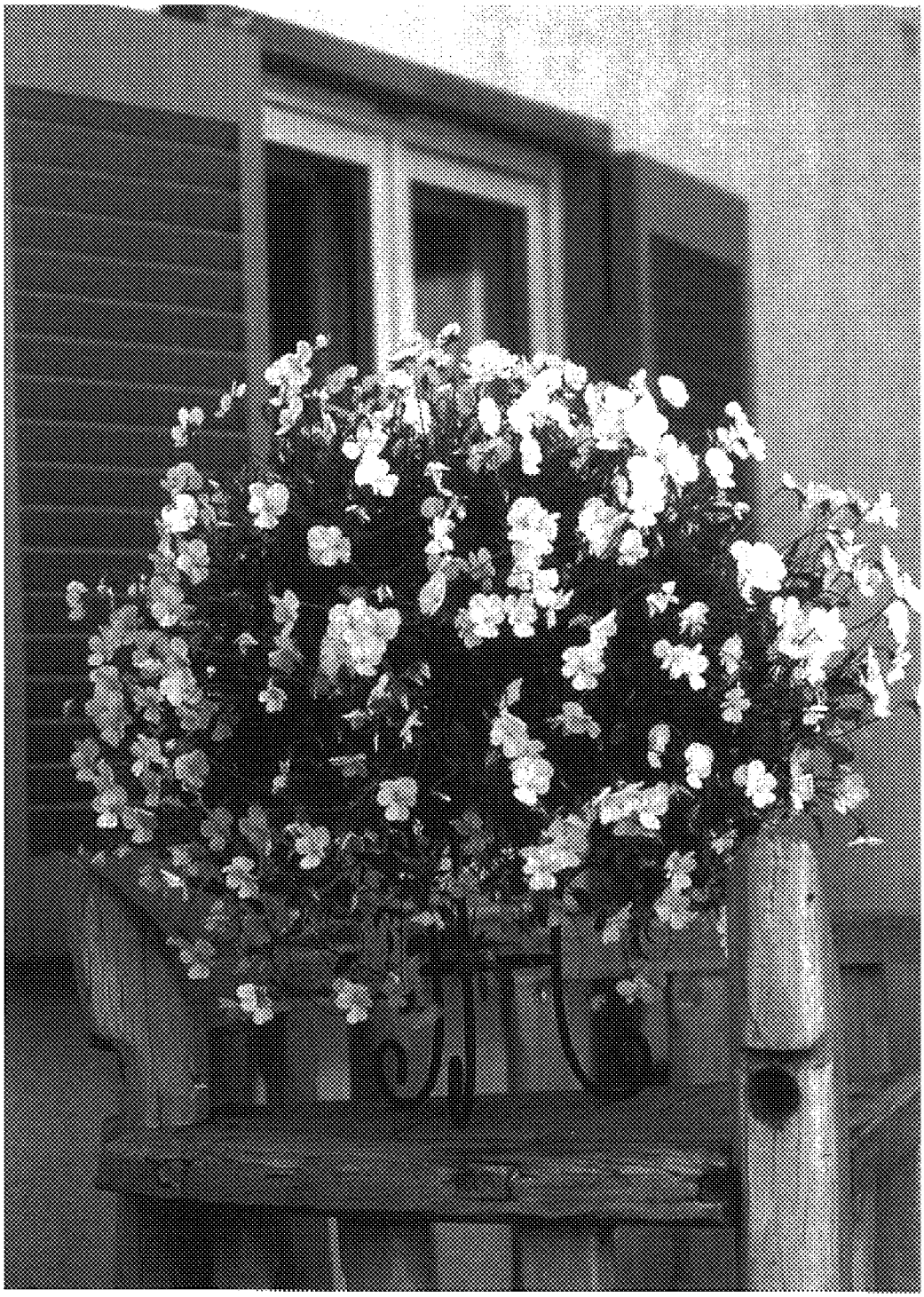
FIG. 1 is a photograph giving a partial view of the new variety of *Viola cornuta* plant 'Sunvioho' planted in pots.
Figure 2:
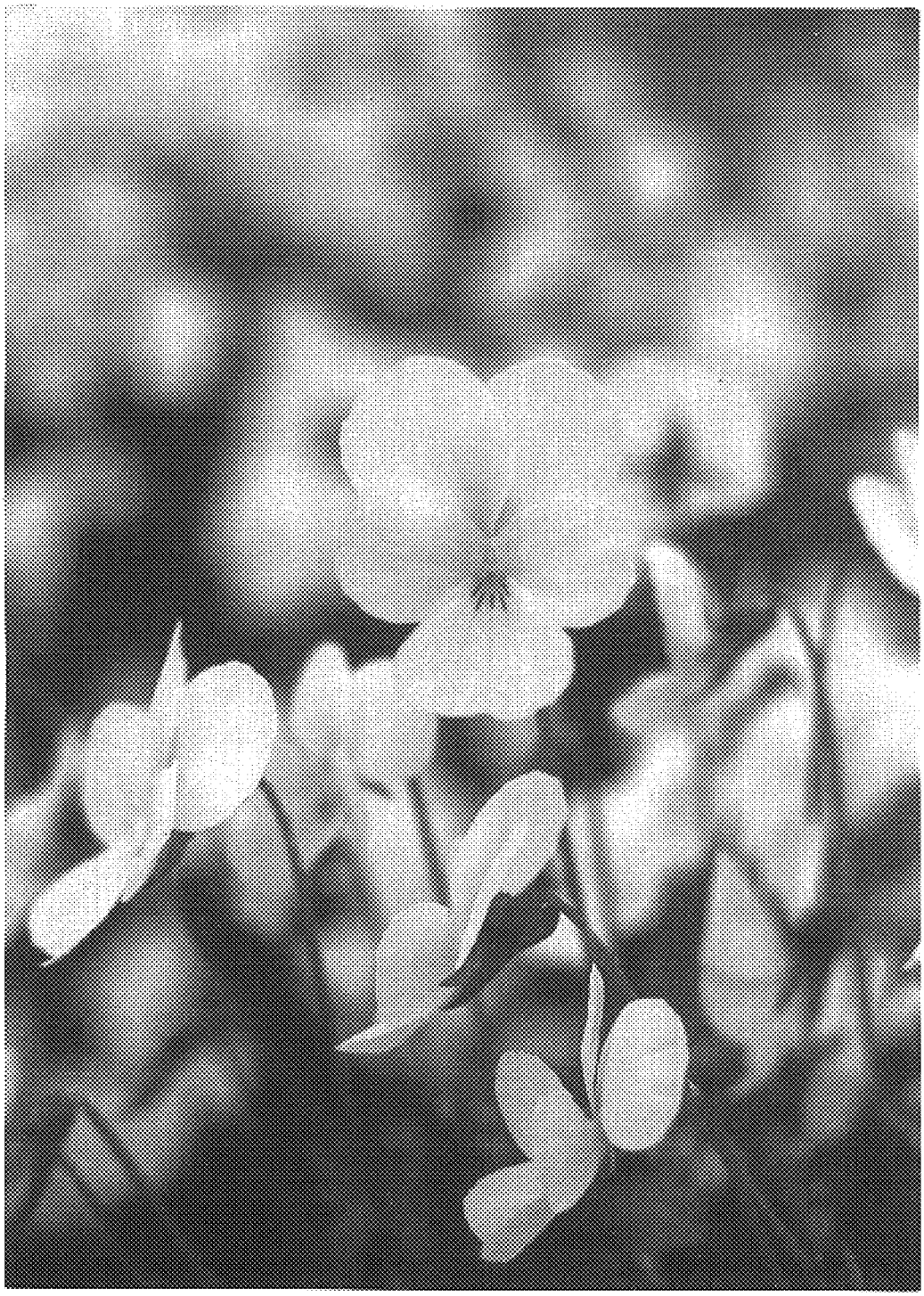
FIG. 2 is a photograph of flowers of the new variety of *Viola cornuta* plant 'Sunvioho'.

The botanical characteristics of this new and distinct variety of *Viola cornuta* plant named 'Sunvioho' are as follows.

Plant:
*Stemmed or non-stemmed.*—Stemmed.
*Growth habit.*—Spreading.
*Height.*—Approximately 10 cm.
*Plant cover.*—Approximately 90 cm.
Stem:
*Length.*—Approximately 50 cm.
*Branching.*—Very abundant branching.
*Pubescence.*—Present.
Leaf:
*Overall form.*—Narrow elliptic.
*Apex form.*—Obtuse.
*Base form.*—Acute.
*Margin.*—Slightly lobed.
*Length.*—Approximately 4.0 cm.
*Width.*—Approximately 2.0 cm.
*Color of upper surface.*—Grayish olive green (Near R.H.S. 137A).
*Color of under surface.*—Moderate yellow green (Near R.H.S. 137C).
*Variegation.*—Absent.
*Leaf luster.*—Matte.
*Vein.*—Apparent.
*Petiole length.*—Approximately 4.0 cm.
*Stipule length.*—Approximately 1.5 cm.
Flower:
*Peduncle length.*—Approximately 12 cm.
*Peduncle thickness.*—Thin.
*Peduncle color.*—Strong yellow green (Near R.H.S. 144A).
*Flower form.*—Vertically oblong.
*Flowering direction.*—Upward.
*Longitudinal diameter.*—Approximately 3.5 cm.
*Horizontal diameter.*—Approximately 2.8 cm.
*Ruffle of petal margin.*—Weakly ruffled.
*Petal curving.*—Weak.
*Number of petals per flower.*—Five (two upper petals, two side petals and one lower petal).
*Time of flowering.*—Early November to June in Japan, except for Hokkaido.
*Lastingness of the individual bloom.*—Approximately 5–7 days.
*Upper petal.*—Form — Round. Size — Approximately 1.7×1.7 cm. Petal color — Single-colored. Ground color — Pale yellow green (Near R.H.S. 157A). Blotch — Absent.
*Side petal.*—Form — Ovate. Size — Approximately 1.5×1.3 cm. Petal color — Single-colored. Ground color — Pale yellow green (Near R.H.S. 157A). Blotch — Absent.
*Lower petal.*—Form — Cordate. Size — Approximately 1.5×1.8 cm. Petal color — Single-colored. Ground color — Pale yellow green (Near R.H.S. 157A). Blotch — Absent.
*Eye color.*—Vivid yellow (Near R.H.S. 13A).
*Eye size.*—Small.
*Thickness of petal.*—Thin.
*Spur length.*—Longer than the sepal appendage.
*Sepal.*—Short.
*Number of flowers.*—Many.
Seed:
*Color.*—Deep brown.
Reproductive organs:
*Stamen.*—Five stamens joined around the ovary. Two lower stamens spurred.
*Stamen length.*—Approximately 2.0 mm.
*Anther color.*—Near R.H.S. 9D (Yellow Group). Tip: near R.H.S. 166B (Greyed-orange group).
*Pollen color.*—Near R.H.S. 9D (Yellow group).
*Pistil length.*—Approximately 4.5 mm.
*Stigma shape.*—Ellipsoidal.
*Stigma length.*—Approximately 1.0 mm.
*Stigma color.*—Near R.H.S. 144B (Yellow-green group).
*Style length.*—Approximately 1.0 mm.
*Style color.*—Near R.H.S. 144D (Yellow-green group).
*Ovary color.*—Near R.H.S. 144C (Yellow-green group).
Physical property:
*Flowering time.*—Early.
*Fragrance.*—Faint or weak.
*Resistance.*—Rain — Strong. This variety as survived temperatures of at least −7° C. The plant grows well at temperatures up to 25° C. Disease — Strong. Pest — Strong.

This new variety of *Viola cornuta* plant 'Sunvioho' is most suitable for flower bedding and potting, hanging basket and ground cover.

COMPARISON WITH SIMILAR VARIETY

The new variety of *Viola cornuta* plant 'Sunvioho' is different from a similar variety, 'Violetto Nive' in following points, 1. The plant width of 'Sunvioho' is wider than that of 'Violetto Nive'.
2. 'Sunvioho' has narrow elliptic leaf while 'Violetto Nive' has lanceolate one.
3. The leaf color of upper surface of 'Sunvioho' is near R.H.S.137A while that of 'Vioetto Nive' is near R.H.S.137B.
4. The longitudinal diameter of 'Sunvioho' is smaller than that of 'Violetto Nive'.

5. The side petal form of 'Sunvioho' is ovate while that of 'Violetto Nive' is round.
6. The flowering time of 'Sunvioho' is early while that of 'Violetto Nive' is intermediate.

The new variety of *Viola cornuta* plant 'Sunvioho' is different from a similar variety, 'Alpine Summer' in following points, 1. The plant width of 'Sunvioho' is wider than that of 'Alpine Summer'.
2. 'Sunvioho' has narrow elliptic leaf while 'Alpine Summer' has lanceolate one.
3. The flowering direction of 'Sunvioho' is upward while that of 'Alpine Summer' is horizontal.
4. The ruffle of petal margin of 'Sunvioho' is weakly ruffled while that of 'Alpine Summer' is flat.
5. 'Sunvioho' has single-colored flower while 'Alpine Summer' has multi-colored one.
6. The color of the upper petal of 'Sunvioho' is near R.H.S. 157A while that of 'Alpine Summer' is near R.H.S. 86B.
7. The color of the side petal of 'Sunvioho' is near R.H.S. 157A while that of 'Alpine Summer' is near R.H.S. 9B with near R.H.S 85B margin and near R.H.S. 79A vein.
8. The color of lower petal of 'Sunvioho' is R.H.S. near 157A while that of 'Alpine Summer' is R.H.S. near 9B with near R.H.S. 79A vein.
9. The flowering time of 'Sunvioho' is early while that of 'Alpine Summer' is intermediate.

What is claimed:

1. A new and distinct variety of *Viola cornuta* plant named 'Sunvioho', substantially as herein illustrated and described.

* * * * *